United States Patent
Park

(10) Patent No.: US 8,241,221 B2
(45) Date of Patent: Aug. 14, 2012

(54) SYSTEMS AND METHODS FOR USE WITH AN IMPLANTABLE MEDICAL DEVICE FOR DETECTING STROKE BASED ON ELECTROCARDIAC SIGNALS

(75) Inventor: Euljoon Park, Valencia, CA (US)

(73) Assignee: Pacesetter, Inc., Sylmar, CA (US)

( * ) Notice: Subject to any disclaimer, the term of this patent is extended or adjusted under 35 U.S.C. 154(b) by 365 days.

(21) Appl. No.: 12/366,526

(22) Filed: Feb. 5, 2009

(65) Prior Publication Data
US 2010/0198082 A1  Aug. 5, 2010

(51) Int. Cl.
*A61B 5/0205* (2006.01)
(52) U.S. Cl. ........ 600/483; 600/301; 600/508; 600/509; 600/513; 600/515; 600/516; 600/517; 600/523
(58) Field of Classification Search .................. 600/301, 600/484, 508–509, 513, 515–517, 523
See application file for complete search history.

(56) References Cited

U.S. PATENT DOCUMENTS

| | | | |
|---|---|---|---|
| 4,485,813 A | 12/1984 | Anderson et al. | |
| 4,535,774 A | 8/1985 | Olson | |
| 4,719,921 A | 1/1988 | Chirife | |
| 4,733,667 A | 3/1988 | Olive et al. | |
| 4,759,366 A | 7/1988 | Callaghan | |
| 4,884,576 A | 12/1989 | Alt | |
| 5,040,533 A | * 8/1991 | Fearnot | 607/22 |
| 5,328,460 A | 7/1994 | Lord et al. | |
| 5,800,467 A | 9/1998 | Park et al. | |
| 6,044,299 A | 3/2000 | Nilsson | |
| 6,050,952 A | 4/2000 | Hakki et al. | |
| 6,208,900 B1 | 3/2001 | Ecker et al. | |
| 6,468,263 B1 | 10/2002 | Fischell et al. | |
| 6,788,970 B1 | 9/2004 | Park et al. | |
| 6,937,896 B1 | 8/2005 | Kroll | |
| 6,961,615 B2 | 11/2005 | Kroll et al. | |
| 7,099,718 B1 | 8/2006 | Thacker et al. | |
| 7,139,609 B1 | 11/2006 | Min et al. | |
| 7,235,530 B2 | 6/2007 | Blair et al. | |
| 7,297,114 B2 | 11/2007 | Gill et al. | |
| 7,502,644 B2 | 3/2009 | Gill et al. | |
| 7,524,287 B2 | 4/2009 | Bharmi | |

(Continued)

OTHER PUBLICATIONS

Afsar, Nazire MD et al., "Acute Stroke Increases QT Dispersion in Patients Without Known Cardiac Diseases," Arch Neurol. 2003;60:346-350.

(Continued)

*Primary Examiner* — Carl H Layno
*Assistant Examiner* — Deborah Malamud

(57) ABSTRACT

Techniques are provided for detecting stroke within a patient using an implantable medical device in conjunction with an external confirmation system. In one example, a preliminary detection of stroke is performed by a subcutaneous monitor based on an analysis of features of an electrocardiogram (ECG) sensed within the patient. Exemplary ECG features indicative of possible stroke include the onset of prominent U-waves, the onset of notched T-waves, and changes in ST segment duration or QT duration or dynamic trends in these parameters. The monitor transmits a signal indicative of possible stroke to a bedside monitor or other external system, which generates a stroke questionnaire for use in confirming the stroke. Family members or other caregivers input answers to the questionnaire into the external system, which confirms or disconfirms the stroke. Emergency personnel can be automatically notified. Implantable systems that detect stroke based on intracardiac electrogram (IEGM) signals are also described herein.

18 Claims, 8 Drawing Sheets

U.S. PATENT DOCUMENTS

2006/0100530 A1    5/2006    Kliot et al.
2007/0032736 A1    2/2007    Finnigan et al.
2007/0276270 A1*   11/2007   Tran .............................. 600/508

OTHER PUBLICATIONS

Bozluolcay, M. et al., Electrocardiographic findings and prognosis in ischemic stroke, Neurology India. 2003;51(4):500-502.

Carrera, E. MD et al., "Continuous assessment of electrical epileptic activity in acute stroke," Neurology. 2006;67:99-104.

Christensen, Hanne et al., "Abnormalities on ECTG and telemetry predict stroke outcome at 3 months," Journal of Neurological Sciences. 2005;234(1):99-103.

Dash, Monali et al., "ECG Changes in Pediatric Patients with Severe Head Injury," Journal of Neurosurgical Anethesiology. 2003;15(3):270-273.

Finnigan, Simon P. et al., "Quantitative ECG indices of sub-acute ischaemic stroke correlate with clinical outcomes," Clinical Neurophysiology. 2007;118:2525-2532.

Finnigan, Simon P. et al., "Correlation of Quantitative ECG in Acute Ischemic Stroke With 30-Day NIHSS Score—Comparison With Diffusion and Perfusion MRI," Stroke. 2004;35-899-903.

Hossmann, K.-A. et al., "EEG Frequency Analysis in the course of Acute Ischemic Stroke," Neurosurg. Rev. 1980;3:31-36.

Hu, Xiao et al., "An algorithm for extracting intracranial pressure latency relatve to electrocardiogram R wave," Physiol. Meas. 2008;29:459-471.

Hwa, Rodolph C. et al., "Stroke detection based on the scaling properties of human EEG," Physica A. 2004;338:246-254.

Jachuck, S.J. et al., "Electrocardiographic Abnormalities Associated with Raised Intracranial Pressure," British Medical Journal. 1975;1:242-244.

Kanter, Merrill C. MD et al., "Carotid Stenosis in Patients With Atrial Fibrillation—Prevalence, Risk Factors, and Relationship to Stroke in the Stroke Prevention in Atrial Fibrillation Study," Arch Intern Med. 1994;154-1372-1377.

Krul, J.M. et al., "Stroke-related EEG Changes During Carotid Surgery," Eur J Vasc Surg. 1989;3:423-428.

Oppenheimer, Stephen MD, FRCP, "Neurogenic cardiac effects of cerebrovascular disease," Current Opinion in Neurology. 1994;7:20-24.

Van Putten, Michel J.A.M. MD, PhD et al., "Continuous Quantitative EEG Monitoring in Hemispheric Stroke Patients Using the Brain Symmetry Index," Stroke. 2004;35:2489-2492.

Grmec, S. et al., "Electrocardiographic changes in patients with acute stroke in the prehospital setting and their prognostic importance," Critical Care. 2006;10(Supp.1):457.

Hoshide, Satoshid MD et al., "Marked Elevation of the Segment in Cerebellar Hemorrhage," JAGS. 2005;53(10):1837-1349.

NIH, NIH Stroke Scale, National Institutes of Health, www.ninds.nih.gov/doctors/NIH_Stroke_Scale.pdf.

Ruel, Marc MD, MPH et al., "Late Incidence and Determinants of Stroke After Aortic and Mitral Valve Replacement," Ann Thorac Surg. 2004;78:77-83.

Sacco, Ralph L. MD et al., "Guidelines for Prevention of Stroke in Patients with Ischemic Stroke or Transient Ischemic Attach," Stroke. 2006;37:577-617.

Sakr, Yasser L. et al., "Relation of ECG changes to neurological outcome in patients with aneurysmal subarachnoid hemorrhage," International Journal of Cardiology. 2004;96:369-373.

Schuchert, A. et al., "Impact of Long-Term ECG Recording on the Detection of Paroxysmal Atrial Fibrillation in Patients After an Acute Ischemic Stroke," Pace. 1999;22:1082-1084.

Smith, McKamy MD et al., "Cardiac Arrhythmias, Increased Intracranial Pressure, and the Autonomic Nervous System," Chest. 1972;61(2)125-133.

Tobis, Jonathan M. MD, et al. "Does Patent Foramen Ovale Promote Cryptogenic Stroke and Migraine Headache?" Tex Heart Inst J. 2005;32(3):362-365.

* cited by examiner

SYSTEMS AND METHODS FOR USE WITH AN IMPLANTABLE MEDICAL DEVICE FOR DETECTING STROKE BASED ON ELECTROCARDIAC SIGNALS

FIELD OF THE INVENTION

The invention generally relates to implantable medical devices, such as pacemakers, implantable cardioverter/defibrillators (ICDs) and subcutaneous implantable monitors, and, in particular, to techniques for detecting stroke within patients in which such devices are implanted.

BACKGROUND OF THE INVENTION

A stroke is a sudden loss of brain function caused by a blockage of a blood vessel to the brain (ischemic stroke) or a rupture of a blood vessel to the brain (hemorrhagic stroke). Each year, more than 700,000 people in the U.S. alone suffer a new or recurrent stroke and the consequences can be devastating. Over 150,000 of these events end in death, and many of those who survive are left seriously and permanently impaired. During each minute of progression of a stroke, about two million brain cells die. Approximately fourteen billion brain cells die during the average ten-hour stroke. As such, the time from onset of a stroke to its diagnosis and treatment by medical personnel is critical.

Accordingly, it would be highly desirable to provide techniques for detecting the onset of a stroke within a patient for promptly notifying family members, caregivers or emergency personnel, and it is to that end that the invention is generally directed.

SUMMARY OF THE INVENTION

In an exemplary embodiment, a method is provided for use with an implantable medical device for implant within a patient. The method includes: sensing electrocardiac signals using the implantable device and then detecting an indication of stroke within the patient based on predetermined changes in the electrocardiac signal. Exemplary changes within an electrocardiac signal indicative of stroke include the onset of prominent U-waves, the onset of notched T-waves, changes in ST segment duration, and changes in QT duration and/or any dynamic changes (trends) in time in any of these signals. These are just some examples. In general, any of a variety of predetermined changes in the electrogram indicative of stroke can be exploited (and/or predetermined dynamic changes/trends in time can be exploited.) Such changes/trends can be detected, for example, using an electrocardiogram (ECG) signal sensed using a subcutaneous loop/recorder monitor or other suitable implantable device.

In an illustrative embodiment, the implantable device could be used in conjunction with an external display system such as a bedside monitor. The implantable device detects a preliminary indication of a possible stroke based on the electrocardiac signals and transmits a signal indicative of possible stroke to the external system. The external system then generates a questionnaire for display to family members or caregivers of the patient for confirming the stroke. Answers to the questionnaire are input into the external system, which confirms the stroke based on the answers. If the stroke is confirmed, suitable warning signals are provided to the family members or caregivers. In some instances, emergency personnel are automatically notified via a suitable telephonic or computer network communication system. The patient's primary care physician can also be directly notified. In this manner, medical attention can promptly be provided to reduce the risk of death or permanent impairment due to the stroke.

The questionnaire preferably includes simple questions that can be quickly answered by the patient's family or caregiver for confirming the stroke. In one particular example, a short questionnaire is used that includes questions drawn from (or based on) a five element stroke questionnaire provided by the "The Stroke Collaborative," which is a joint campaign of the American Academy of Neurology, the American College of Emergency Physicians, and the American Heart Association/American Stroke Association. Briefly, five questions are provided that are directed to patient balance, speech, weakness/numbness, vision and severity of headache.

In other examples, a more detailed questionnaire is used to provide a more comprehensive and quantitative measure of stroke-related neurologic deficit, such as questions to evaluate the effect of acute cerebral infarction on the levels of consciousness, language, neglect, visual-field loss, extraocular movement, motor strength, ataxia, dysarthria, and sensory loss. In one such example, the detailed questionnaire includes questions drawn from the National Institutes of Health Stroke Scale (NIHSS) questionnaire or other suitable stroke score questionnaires.

The external system confirms the stroke and, in some examples, can also evaluate its severity. In some particular examples, automatic notification of emergency personnel is triggered based on the severity of the stroke.

One particular advantage of using a stroke questionnaire to confirm the stroke is that some of the predetermined changes/trends in the ECG used to detect the onset of a stroke might also occur for other reasons. Cardiac ischemia, e.g., can produce changes in ST segment duration and in QT duration. The questionnaire can thereby help distinguish stroke from cardiac ischemia. In some examples, if the answers to the stroke questionnaire disconfirm the stroke, suitable warnings as to cardiac ischemia can instead be issued. Also, in some examples, either the implanted device or the external system can attempt to automatically distinguish stroke from cardiac ischemia based on an analysis of the predetermined ECG changes/trends. The use of the questionnaire is preferred since any distinction based solely on the ECG might not be entirely reliable, at least for some patients. Nevertheless, circumstances may arise where the automatic discrimination of stroke from other medical conditions is warranted, particularly if no one is available to answer the questions in the stroke questionnaire.

In still other examples, the preliminary detection of stroke is based on an intracardiac electrogram (IEGM) signal detected by a pacemaker/ICD, rather than an ECG detected by a subcutaneous monitor. In some cases, therapy might be directly controlled or adjusted by the implantable device based, at least in part, on an electrocardiac signal-based stroke detection. Method and system examples are described in detail below.

BRIEF DESCRIPTION OF THE DRAWINGS

The above and further features, advantages and benefits of the invention will be apparent upon consideration of the descriptions herein taken in conjunction with the accompanying drawings, in which.

DETAILED DESCRIPTION OF THE PREFERRED EMBODIMENTS

The following description includes the best mode presently contemplated for practicing the invention. This description is not to be taken in a limiting sense but is made merely to describe general principles of the invention. The scope of the invention should be ascertained with reference to the issued claims. In the description of the invention that follows, like numerals or reference designators are used to refer to like parts or elements throughout.

Overview of ECG-Based Stroke Detection System

Figure 1:
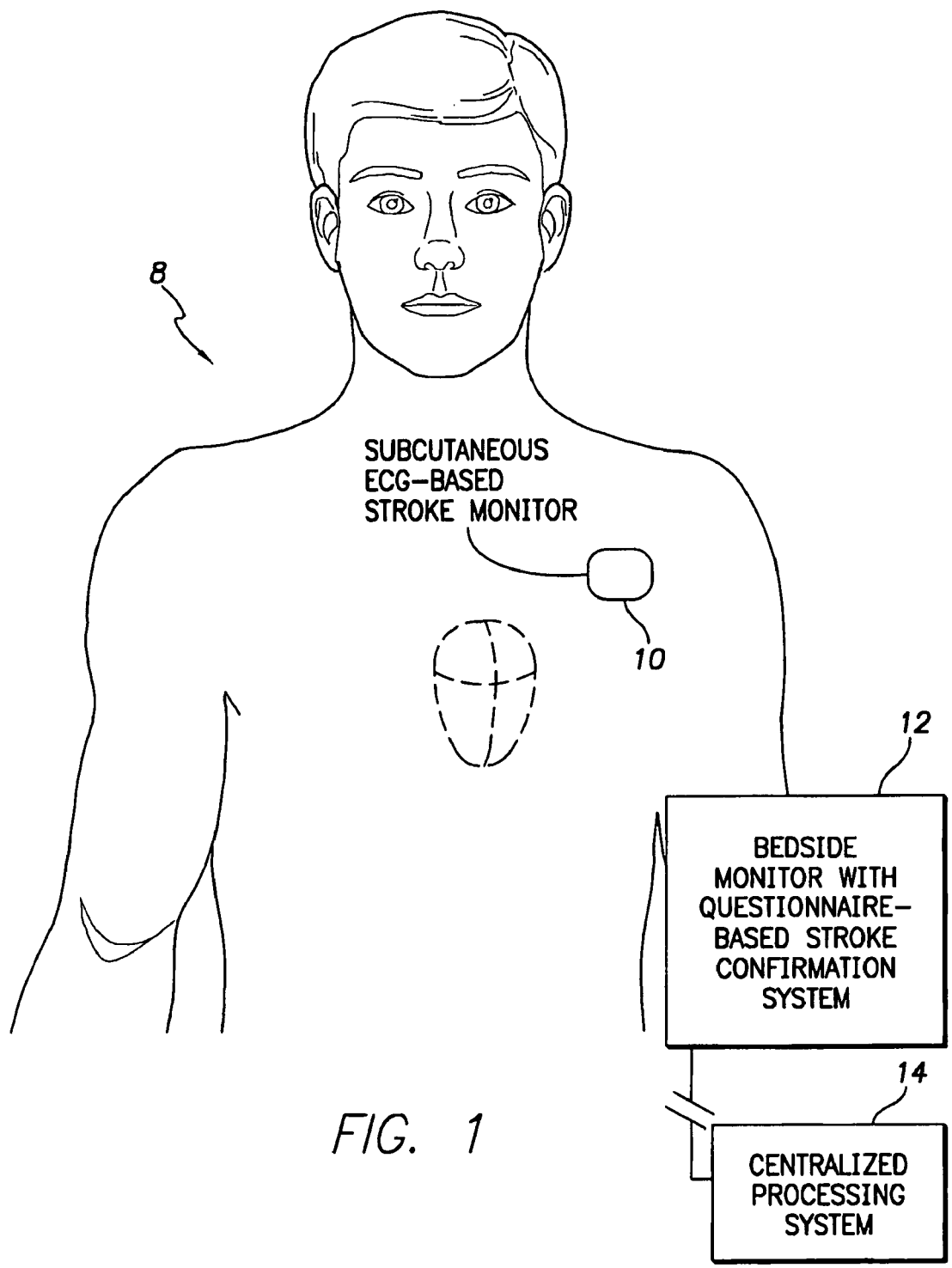
FIG. 1 illustrates pertinent components of a subcutaneous ECG-based monitor system capable of detecting the onset of a stroke in conjunction with an external bedside monitor-based stroke confirmation system.

Referring first FIG. 1, a broad overview of components of an exemplary embodiment of the invention will now be provided. Briefly, FIG. 1 illustrates an ECG-based stroke detection system 8 having a subcutaneously-implanted stroke monitor 10 for detecting a stroke within the patient based on an analysis of ECG signal and an external bedside monitor 12 for confirming the stroke and/or for generating suitable warning signals. In a preferred embodiment, the implanted stroke monitor 10 makes a preliminary detection of the onset of stroke based on an analysis of the ECG signals sensed via electrodes mounted to the housing of the stroke monitor and then transmits an indicator signal to the bedside monitor, which operates to confirm the stroke based on answers by family members or caregivers to a stroke questionnaire presented using the bedside monitor. The bedside monitor then alerts the family members or caregivers of the stroke and also forwards warning signals or other suitable information via a centralized processing system 14 to the patient's primary care physician or, in some implementations, directly to emergency personnel. The centralized system may include such systems as the HouseCall™ system or the Merlin@home/Merlin.Net systems of St. Jude Medical.

In other implementations, rather than relying a questionnaire to confirm the stroke, the implanted stroke monitor and/or bedside monitor detects the stroke solely based on the ECG signals/trends. This is appropriate in circumstances where answers to the stroke questionnaire are not readily forthcoming (such as if no family members or caregivers are immediately available to answer the stroke questionnaire) or if changes in the patient's ECG are so distinctive of stroke that further confirmation via the stroke questionnaire is unnecessary and might unduly delay notifying emergency personnel.

Overview of ECG-Based Stroke Detection Techniques

Figure 2:
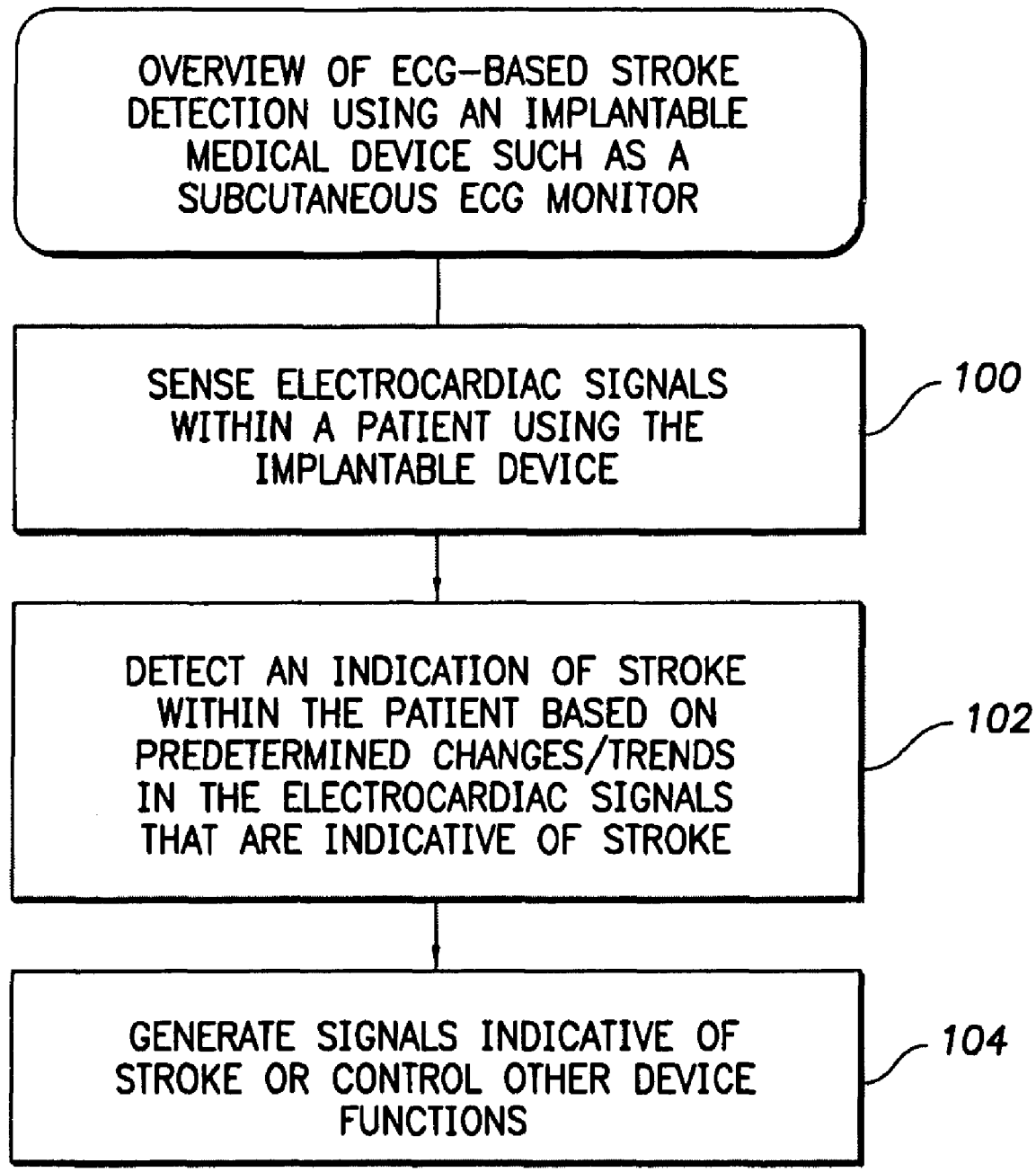
FIG. 2 provides an overview of the method for detecting stroke performed by the system of FIG. 1, which exploits predetermined changes/trends in an electrocardiac signal indicative of stroke.

FIG. 2 provides a broad overview of the ECG-based stroke detection techniques of the invention. Initially, at step 100, ECG or other electrocardiac signals are sensed or detected within a patient using an implantable medical device, such as a subcutaneous loop recorder/monitor. At step 102, an indication of stroke is detected within the patient based on predetermined changes or trends in the electrocardiac signals indicative of stroke. In this regard, whether ischemic or hemorrhagic, strokes are known to produce changes in the ECG of a patient. These ECG changes appear to be due to extreme sympathetic neural stimulation associated with stroke, which in turn may be associated with raised intracranial pressures (ICPs) arising due to the stroke. In this regard, augmentation of intra-cardiac sympathetic nerve activity seems to occur, producing cardiac myocyte damage and depolarizing ionic shifts, resulting, e.g., in ECG repolarization changes. Nevertheless, regardless of the physiological mechanism by which the stroke causes changes in the ECG, these changes (or trends therein) can be detected to provide an indication of stroke.

Exemplary changes in the ECG indicative of stroke include the onset of prominent U-waves, the onset of notched T-waves, changes in ST segment duration, and changes in QT duration within an ECG and/or any dynamic changes (trends) in time in any of these signals. (As already noted, these are just some examples. In general, any of a variety of predetermined changes in the electrogram and/or predetermined dynamic changes/trends in time can be exploited.) U-waves are thought to represent electrical repolarization of the papillary muscles or Purkinje fibers. U-waves are not always present in the ECG but can become prominent during a stroke. The T-wave of the ECG corresponds to a cardiac ventricular repolarization event, i.e. it is an electrical signal produced during the repolarization of the ventricular myocardium following a ventricular contraction triggered by ventricular depolarization. The T-wave follows a ventricular depolarization event known as an R-wave or QRS-complex. T-waves are usually smooth in shape, but stroke can cause notches to appear within the T-waves. Herein, the ST segment refers to the interval from the end of the QRS-complex to the beginning of the subsequent T-wave. The QT interval refers to the interval from the start of the QRS-complex to the beginning of the T-wave. These and other morphological features of the ECG can be detected, for example, using the ECG signal sensed by an implantable monitor or other suitable implantable medical device. (Note that the ECG sensed by a subcutaneous device can differ somewhat from that of a surface ECG sensed by a set of surface-mounted electrodes. Nevertheless, morphological features corresponding to those of a surface ECG can usually be identified within the subcutaneously-sensed ECG.)

At step 104, the implantable device generates signals indicative of stroke (such as by generating a preliminary stroke indication signal for transmission to a bedside monitor for confirmation) or controls other device functions (such as by generating warning signals for alerting the patient using an implanted alarm device if one is provided, or recording suitable diagnostic data within internal memory.)

Overview of Stroke Questionnaire-Based Confirmation Techniques

Figure 3:
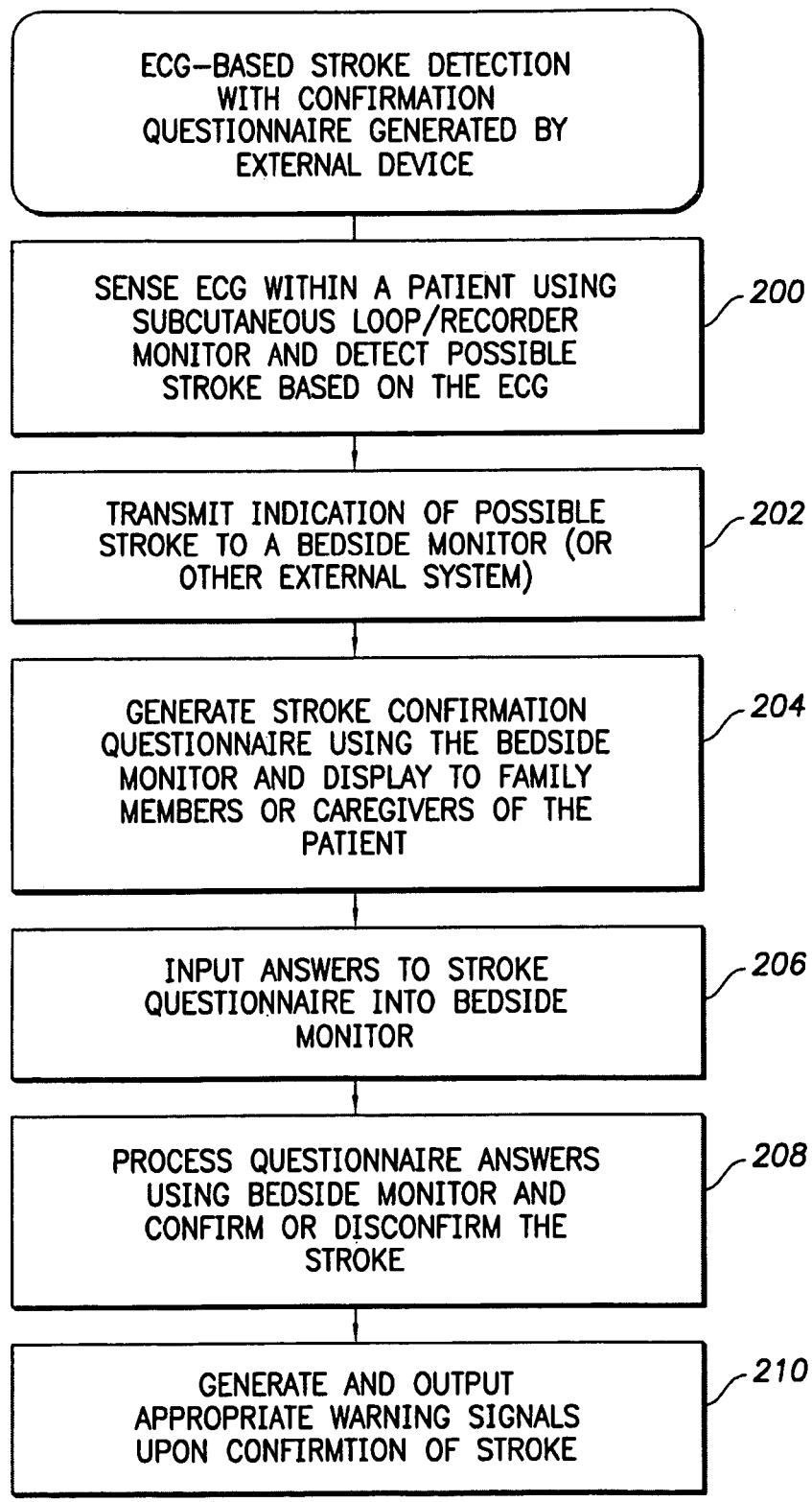
FIG. 3 illustrates an exemplary embodiment of the general technique of FIG. 2, wherein a preliminary detection of stroke by the subcutaneous implantable monitor is confirmed based on a stroke questionnaire generated by a bedside system or other external system.

FIG. 3 provides an overview of an ECG-based stroke detection technique wherein confirmation is provided via a stroke questionnaire using a bedside monitor or other external device. Initially, at step 200, the implantable medical device senses the ECG within a patient and detects a possible stroke based on an analysis of the ECG, as discussed above. At step 202, the implantable medical device transmits an indication of possible stroke to the bedside monitor (or other external confirmation system.) At step 204, the bedside monitor generates a stroke confirmation questionnaire and displays the questionnaire to family members or caregivers of the patient. The questionnaire includes questions intended to provide for an assessment of any stroke-related mental impairment for use in confirming the stroke. A very simple questionnaire is preferred that lay people can easily ask, answer and understand. In one particular example, the bedside monitor issues a loud alarm to notify family members or caregivers of a possible stroke within the patient. The family members or caregivers then read and answer the questions within the stroke questionnaire while observing the patient and, if the patient is sufficiently alert, while also talking to the patient.

At step 206, the bedside monitors inputs answers to the stroke questionnaire via a keyboard or other suitable input device. That is, the family members or caregivers directly type answers to the stroke questionnaire into the bedside monitor. Depending upon the particular implementation, the bedside monitor may be equipped to display a set of "multiple choice" answer boxes that the family member of caregiver can simply select using a mouse. In still other implementations, the bedside monitor may be equipped to speak the questions aloud and to receive, understand and record voice responses. In any case, at step 208, the bedside monitor processes the questionnaire answers to confirm or disconfirm the stroke. Depending upon the particular questionnaire, each answer may be assigned a numerical value and the bedside monitor then sums the values to generate a "stroke score," which is compared against a threshold. If the score exceeds a predetermined numerical threshold, stroke is thereby confirmed. Otherwise, stroke is disconfirmed. In other implementations, any affirmative answer to the stroke questionnaire (indicative of a stroke-related deficit within the patient) is sufficient to confirm the stroke.

At step 210, the bedside monitor then generates and outputs appropriate warning signals upon confirmation of a stroke. The warning signals are provided to the family members or caregivers and can also be relayed to the patient's primary care physician or directly to emergency personnel such as, e.g., by directly calling 911 or other suitable emergency telephone numbers. For a severe stroke, direct notification of emergency personnel is preferred so as to achieve the quickest possible response. As already noted, about two million brain cells can die during each minute of progression of a stroke and so prompt medical attention is crucial.

Exemplary Stroke Confirmation

Figure 4:
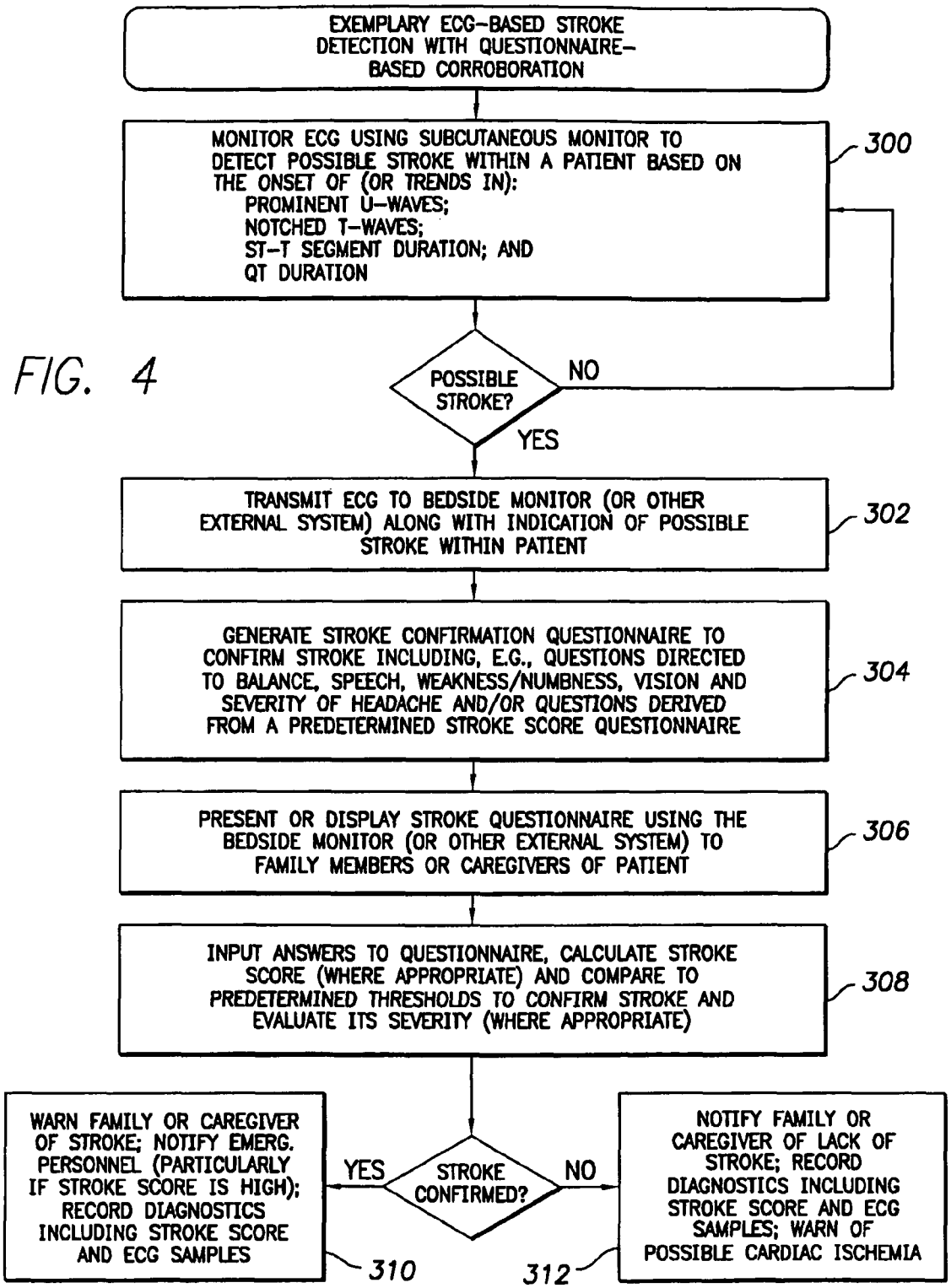
FIG. 4 provides a more detailed illustration of the technique of FIG. 3, particularly identifying ECG parameters employed by the subcutaneous implantable monitor to detect a preliminary indication of stroke as well as questionnaire topics exploited by the bedside monitor to confirm the stroke.

FIG. 4 provides a more detailed example of ECG-based stroke detection with questionnaire corroboration. At step 300, an implantable subcutaneous device monitors the ECG of the patient in which the device is implanted to detect possible stroke within a patient based on the onset of (or trends in): prominent U-waves; notched T-waves; ST segment duration; and QT duration. Otherwise conventional morphological event detection techniques may be used by the device to detect these features of the ECG and quantify their size and/or duration. For U-waves, the device examines the portion of the ECG where U-waves are expected to be found and, if U-waves are detected, the device then measures and quantifies the size and duration of the U-wave. For T-waves, the device examines the T-wave to detect any notches and, if present, measures and quantifies the depth and duration of the notches. For ST segment duration and QT duration, the device measures any changes in the duration of these intervals, either shortening or lengthening.

Once these or other ECG features indicative of a possible stroke are detected, the implantable device compares the measured parameters against pre-determined thresholds indicative of stroke. Otherwise routine experimentation can be performed to identify, for each parameter, one or more suitable thresholds for use in detecting a preliminary indication stroke. The thresholds may then be adjusted in view of baseline values obtained within the particular patient and updated periodically. Then, if all (or some) of the parameters exceed their respective thresholds, a preliminary indication of stroke is thereby generated. In some implementations, only a single parameter needs to exceed its threshold to trigger a preliminary indication of stroke. In other implementations, to avoid "false positives," two or more features are required to exceed their respective features. It is believed that the sudden onset of prominent U-waves or notched T-waves is particularly indicative of stroke and, hence, these features by themselves typically warrant a preliminary indication of possible stroke. Changes in ST segment duration and QT duration can also occur during cardiac ischemia (or due to changes in medication) and hence these parameters are used, at least in some implementations, only in combination with prominent U-waves or notched T-waves. Also, at step 302, trends in any of these parameters can be tracked and exploited. For example, the rate of change of ST segment duration or QT duration can be exploited, rather than merely their absolute values.

Assuming a possible stroke has been detected then, at step 302, the device transmits the patient's ECG to the bedside monitor (or other external stroke confirmation system) along with a signal or value indicating possible stroke within the patient. Depending upon the implantation, the telemetry signals are transmitted directly from the implanted device to the bedside monitor or other external device. In other implementations, a telemetry wand or other portable relay device may be exploited to aid in routing signals from the implanted device to the bedside monitor. Given that the patient might be incapacitated by the stroke, relatively long-range telemetry capability is preferred to ensure the signals are received by the bedside monitor or other external stroke confirmation system.

At step 304, the bedside monitor (or a remote system connected thereto) then generates a stroke confirmation questionnaire to confirm the stroke. In one particular example, the questionnaire includes brief questions directed to balance, speech, weakness/numbness, vision and severity of headache. These questions may be drawn from (or based on) those of a stroke questionnaire provided by the aforementioned "The Stroke Collaborative," which is currently described at http://www.giveme5forstroke.org.

Some exemplary specific questions based on those of The Stroke Collaborative questionnaire will now be listed. However, no claim in made herein as to any intellectual property rights to the questions themselves.

(1) BALANCE: IS THE PATIENT'S BALANCE OFF?
(2) SPEECH: IS THE PATIENT'S SPEECH SLURRED OR IS THE PATIENT'S FACE DROOPED?
(3) WEAKNESS/NUMBNESS: IS ONE SIDE THE PATIENT WEAK OR NUMB?

(4) VISION: IS THE PATIENT'S VISION IMPAIRED?
(5) HEADACHE: DOES THE PATIENT HAVE A SEVERE HEADACHE?

If any of these questions is answered in the affirmative, the stroke is thereby confirmed.

Alternatively, at step 304, a more detailed questionnaire is generated to provide a more quantitative measure of stroke-related neurologic deficit, including questions directed to evaluating the effect of acute cerebral infarction on levels of consciousness, language, neglect, visual-field loss, extraocular movement, motor strength, ataxia, dysarthria, and sensory loss, such as a questions drawn from the NIHSS questionnaire or other stroke score questionnaires. The NIHSS questionnaire currently may be found via the National Institutes of Health website: http://www.nih.gov. Other exemplary questionnaires that might be exploited include the Barthel Index, the Glasgow Outcome Scale, the Hunt and Hess Classification of Subarachnoid Hemorrhage, the Modified Rankin Scale, The Birmingham Regional Emergency Medical Services System, the Cincinnati Prehospital Stroke Scale, the Dallas Stroke Council Stroke Evaluation Sheet, Los Angeles Prehospital Stroke Screen protocol, and the Miami Emergency Neurologic Deficit (MEND) Prehospital Checklist.

Note that, for use by family members, the various questionnaires may be rewritten or simplified so as to not require any expert medical knowledge by, for example, eliminating medical jargon and providing more "user friendly" questions. In general, a very simple questionnaire is preferred, which lay people can easily ask, answer and understand.

As already noted the bedside monitor displays the questions or reads them aloud so that the questions can be answered by family members or caregivers. In other cases, the family members or caregivers are given a hard-copy of the questionnaire in advance so they may simply read the questions and input the answers. In other implementations, an interactive questionnaire is provided via the Merlin@home system. Questionnaire answers can be correlated with subsequent stroke diagnosis made by medical professionals to improve the sensitivity/specificity/positive predictive value (PPV)/negative predictive value (NPV) of any questionnaire-based stroke detection methods.

At step 308, the bedside monitor inputs the answers to the questionnaire and then, where appropriate, calculates a stroke score for the patient. (Some questionnaires, such as the five element questionnaire presented above, do not necessarily provide for a stroke score.) In implementations where a score is generated, the score is compared to predetermined thresholds to confirm or disconfirm the stroke and evaluate its severity. Thresholds indicative of stroke severity as measured by the NIHSS scoring system are:

0=no stroke
1-4=minor stroke
5-15=moderate stroke
15-20=moderate/severe stroke
21-42=severe stroke With the NIHSS scale, any score of 1 or above indicates some level of stroke. With the five element test listed above, any affirmative answer is indicative of some level of stroke.

In some implementations, emergency personnel are only notified for moderate to severe strokes (if the questionnaire is sufficient to ascertain the severity of the stroke.) Also, in some implementations, an initial baseline score is recorded for the patient in advance for comparison. Then, upon detection of a possible stoke, the new stroke score for the patient is compared against the baseline. The stroke is confirmed only if the new score is at least somewhat higher than the baseline score. Also, it should be understood that the bedside monitor need not wait until the entire stroke questionnaire has been answered to confirm the stroke. Rather, as soon as enough questions have been answered to confirm the stroke, the bedside monitor can take action. As can be appreciated, a variety of different protocols and procedures may be used for confirming strokes, ranking their severity and triggering responses and no attempt is made herein to itemize all possible examples.

If the stroke is confirmed then, at step 310, the bedside monitor warns the family or caregivers of the stroke using suitable audible or visual signals or displays; notifies emergency personnel (particularly if the stroke score is high); and records diagnostics, including the stroke score (where generated) and ECG samples for review by the emergency personnel or physicians. Conversely, if the stroke is not confirmed then, at step 312, the bedside monitor notifies the family or caregivers of the lack of stroke; records suitable diagnostics; and warns of possible cardiac ischemia. In this regard, some of the parameters indicative of stroke, particularly changes in ST segment duration or QT duration, can also be indicative of cardiac ischemia. Hence, the family members or caregivers can be warned of the possible cardiac ischemia so that medical attention can be sought, if needed.

In some implementations, either the implanted device or the bedside monitor can be programmed to automatically attempt to distinguish stroke from cardiac ischemia based on an analysis of the ECG of the patient so that appropriate warnings can be given. For example, if notched T-waves and prominent U-waves are detected, but no changes in ST segment duration or QT duration are detected, the condition is deemed to be stroke. Conversely, if changes in ST segment duration and QT duration are detected, but notched T-waves and prominent U-waves are not detected, then the condition is deemed to be a possible cardiac ischemia. Still other morphological parameters of an ECG (or IEGM, if available) can be exploited to detect and distinguish cardiac ischemia. See, for example, U.S. patent application Ser. No. 12/016,166 of Boileau et al., filed Jan. 17, 2008, entitled "Systems and Methods for Distinguishing Cardiac Ischemia from Systemic Influences on IEGM Morphology using an Implantable Medical Device." See also, U.S. patent application Ser. No. 11/394,724, of Ke et al., filed Mar. 31, 2006, entitled "Ischemia Detection using T-wave Amplitude, QTmax and ST Segment Elevation and Pattern Classification Techniques."

The above-described techniques can be implemented with a variety of implantable medical devices in combination with a variety of external systems. In one particular implementation, the implantable medical device includes or comprises a Confirm™ monitor provided by St. Jude Medical. This device is adapted for subcutaneous implant, particularly within patients suspected of suffering episodes of atrial fibrillation (AF.) The device is thus preferably equipped to detect both AF (and other possible arrhythmias) as well as possible stroke. AF increases the risk of ischemic stroke due to thrombosis and so the incorporation of stroke monitoring with a subcutaneous AF monitor is highly desirable.

Exemplary Subcutaneous Implantable Monitor with AF and Stroke Detection

Figure 5:
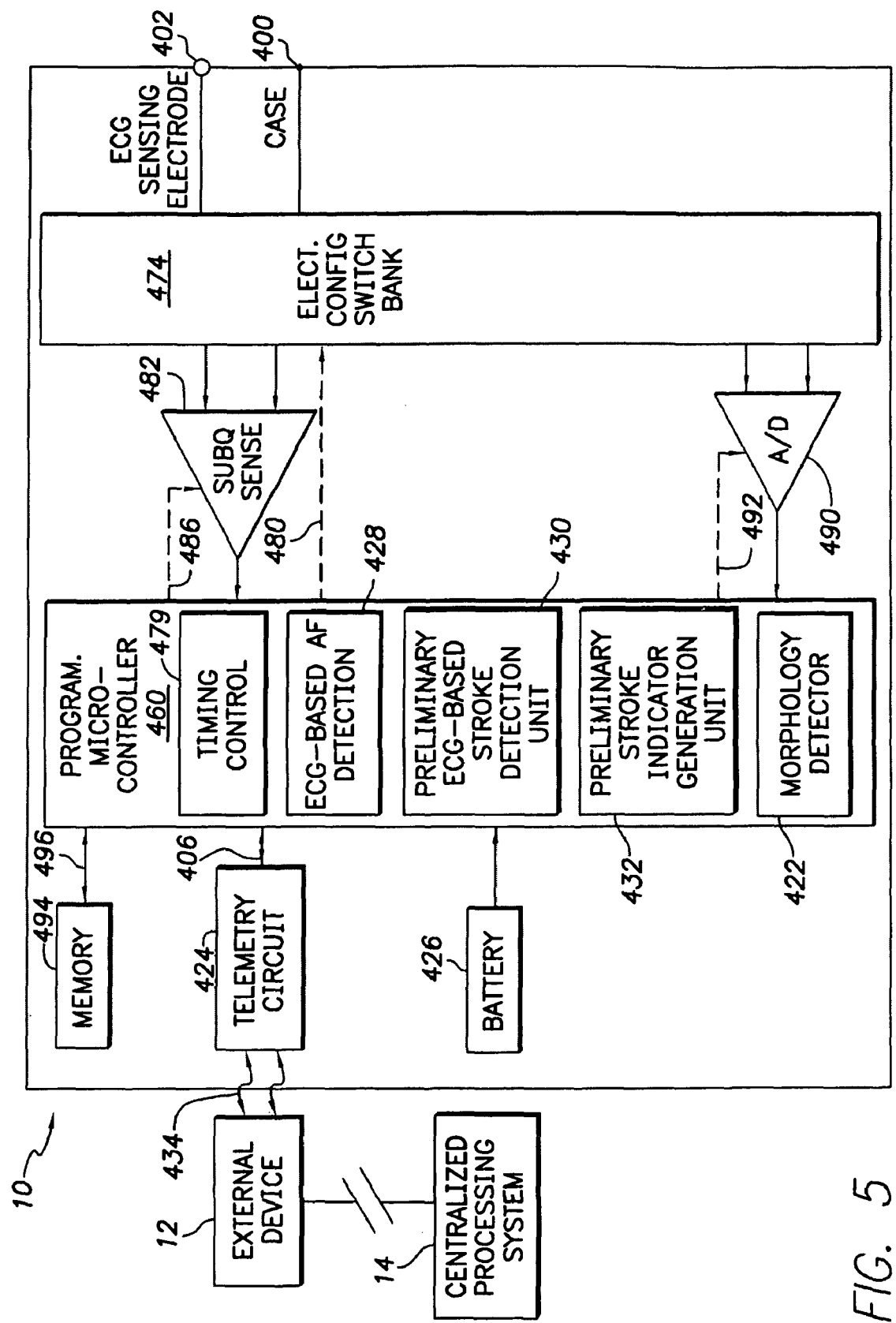
FIG. 5 is a functional block diagram of selected components of the subcutaneous implantable monitor of FIG. 1 for detecting a preliminary indication of stroke based on ECG signals.

For the sake of completeness, internal components of an exemplary implantable monitor for use as stroke monitor 10 of FIG. 1 will now be summarized with reference to FIG. 5. This device is equipped to monitor for AF as well as stroke. Housing 400 (shown schematically) of monitor 10 includes a connector having one or more ECG sensor terminals 402 adapted for connection to subcutaneous (SubQ) ECG sensors mounted to (or connected to) the exterior housing of the device. The housing (often referred to as the "can", "case" or "case electrode") can also act as the return (common) electrode, or anode, for any sensing electrodes implanted separately from the device. Only one ECG sensing electrode terminal is shown, but additional terminals can be provided to accommodate additional sensing electrodes or sensing leads.

At the core of monitor 10 is a programmable microcontroller 460, which controls AF detection and stroke detection. The microcontroller 460 includes a microprocessor, or equivalent control circuitry, designed specifically for detecting AF and/or stroke and may further include RAM or ROM memory, logic and timing circuitry, state machine circuitry, and I/O circuitry. Typically, the microcontroller 460 includes the ability to process or monitor input signals (data) as controlled by a program code stored in a designated block of memory. The details of the design and operation of the microcontroller 460 are not critical to the invention. Rather, any suitable microcontroller 460 may be used that carries out the functions described herein. The use of microprocessor-based control circuits for performing timing and data analysis functions is well known in the art.

A switch bank 474 includes a plurality of switches for switchably connecting the ECG electrodes (assuming there is more than one) to the appropriate I/O circuits, thereby providing complete electrode programmability. A sense amplifier 482 is coupled to the ECG electrodes through switch bank 474 for detecting electrical cardiac activity. Sense amplifier 482 is capable of sensing signals in accordance with otherwise conventional techniques. The switch bank 474 determines the "sensing polarity" of the cardiac signal by selectively closing the appropriate switches, as is also known in the art. In this way, the clinician may program the sensing polarity. Sense amplifier 482 preferably employs a low power, precision amplifier with programmable gain and/or automatic gain control and/or automatic sensitivity control, bandpass filtering, and a threshold detection circuit, known in the art, to selectively sense electrical signals of interest. The automatic gain control, if implemented, enables the device 10 to deal effectively with the difficult problem of sensing any low frequency, low amplitude signal characteristics. The gain control is actuated by the programmable microcontroller 460. The gains are controlled on sense amplifier 482 by the microcontroller using control line 486. The outputs of the sense amplifier are connected to microcontroller 460.

For AF detection, the invention utilizes the sense amplifier to sense electrical signals to determine whether a cardiac rhythm is physiologic or pathologic. As used herein, "sensing" is reserved for the noting of an electrical depolarization, and "detection" is the processing of sequential sensed depolarization signals potentially in conjunction with the sensor input to establish a diagnosis of an arrhythmia. The timing intervals between sensed events (e.g., P-P intervals) are detected by a timing control unit 479 of microcontroller 460 and then classified by an ECG-based AF detection unit 428 by, for example, comparing the intervals to predefined rate zone limits indicative of AF.

The microcontroller also includes a preliminary ECG-based stroke detection unit 430, which performs the above-described preliminary stroke detection based on ECG morphological parameters (T-waves, U-waves, etc), as detected by a morphology detector 422. A preliminary stroke detection indicator generation unit 432 generates an indication of a possible stroke for relaying to the bedside monitor via a telemetry circuit 424. Collectively, the preliminary ECG-based stroke detection unit and the preliminary stroke detection indicator generation unit provide an "on-board" stroke detector.

ECG signals and other sensed signals are also applied to the inputs of an analog to digital (A/D) data acquisition system 490. The gain of the A/D converter 490 is controlled by the microprocessor 460 by signals along control line 492 in order to match the signal amplitude and/or the resolution to a range appropriate for the function of the A/D converter 490. The data acquisition system 490 is configured to acquire ECG signals, convert the raw analog data into a digital signal, and store the digital signals for later processing and/or telemetric transmission to bedside monitor 12. The data acquisition system 490 is coupled to the ECG electrode 402 through switch bank 474 to sample cardiac signals. The microcontroller 460 is further coupled to a memory 494 by a suitable data/address bus 496, wherein the programmable operating parameters used by the microcontroller 460 are stored and modified, as required, in order to customize the operation of device 10 to suit the needs of a particular patient. Such operating parameters define, for example, the particular parameters to be used to detect stroke or AF.

The operating parameters of implantable device 10 may be non-invasively programmed into the memory 494 through telemetry circuit 424 in telemetric communication with bedside monitor 12 or other external device, such as a programmer, transtelephonic transceiver, or a diagnostic system analyzer. The telemetry circuit 424 is activated by the microcontroller 460 by a control signal 406. The telemetry circuit 424 advantageously allows SubQ ECG electrograms and status information relating to the operation of device 10 (as contained in the microcontroller 460 or memory 494) to be sent to bedside monitor 12 through an established communication link 434, and then on to a centralized processing system 14, where appropriate.

The implantable monitor additionally includes a battery 426 that provides operating power to all of the circuits shown in FIG. 5. The battery is capable of operating at low current drains for long periods of time for monitoring. The battery 426 also should have a predictable discharge characteristic so that elective replacement time can be detected.

Exemplary Bedside Monitor with Stroke Confirmation

Figure 6:
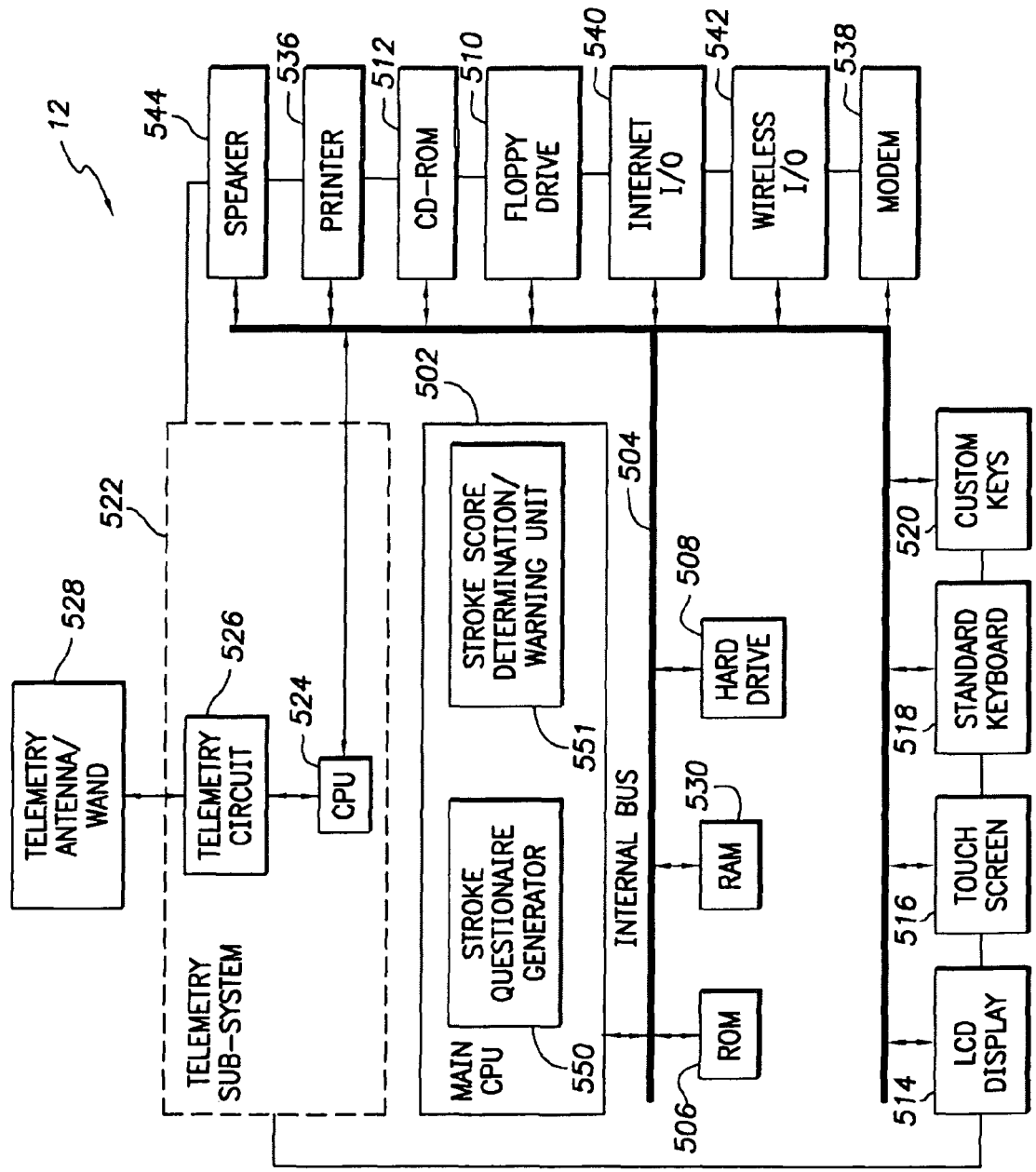
FIG. 6 is a functional block diagram of selected components of the bedside monitor of FIG. 1 for conforming the stroke based answers to the stroke questionnaire.

FIG. 6 illustrates pertinent components of a bedside monitor 12 for use in displaying information received from the implantable monitor of FIG. 5 and for performing the above-described stroke confirmation techniques. Generally, the bedside monitor permits a user (such as a family member of caregiver) to retrieve and display information received from the implantable monitor such as stroke indication signals, ECG data and device diagnostic data. The bedside monitor also displays a stroke questionnaire, inputs questionnaire answers, determines the stroke score for the patient and issues appropriate warning signals, as already described.

Now, considering the components of bedside monitor 12, operations of the bedside monitor are controlled by a CPU 502, which may be a generally programmable microprocessor or microcontroller or may be a dedicated processing device such as an application specific integrated circuit (ASIC) or the like. Software instructions to be performed by the CPU are accessed via an internal bus 504 from a read only memory (ROM) 506 and random access memory 530. Additional software may be accessed from a hard drive 508, floppy drive 526, and CD ROM drive 512, or other suitable permanent mass storage device.

In use, a telemetry antenna or wand 528 operates to receive any signals sent from the implantable monitor, such as the aforementioned preliminary stroke indication signal. Antenna 528 is connected to a telemetry subsystem 522, which includes its own CPU 524 for coordinating the operations of the telemetry subsystem. Main CPU 502 of programmer communicates with telemetry subsystem CPU 524 via internal bus 504. Telemetry subsystem includes a telemetry circuit 526 connected to the telemetry antenna, which, receives and transmits signals electromagnetically from a telemetry unit within the implantable monitor. If a telemetry wand is used, the wand is placed over the chest of the patient near the implantable monitor to permit reliable transmission of data between the telemetry wand and the implantable monitor.

Upon receipt of a preliminary stroke indication signal from the implantable monitor, main CPU 502 displays warning information to the user via an LCD display 514 or other suitable computer display device or other output device (such as a speaker 544) to alert the user to a possible stroke within the patient. The CPU then displays the aforementioned stroke questionnaire, which is generated by a stroke questionnaire generator 550 of the main CPU. The user "interviews" the patient and enters or inputs answers to the questions of the stroke questionnaire via either a touch screen 516 overlaid on the LCD display or through a standard keyboard 518 supplemented by any additional custom keys 520. If so equipped, a stroke score determination/warning unit 551 of the main CPU then calculates a stroke score for the patient and generates any warning signals, such as warnings issued to the user via speaker 544 or warnings issued to the patient's physician or to emergency personnel via an Internet input/output (I/O) unit 540, a wireless I/O unit 542, a modem 538 or other suitable I/O system to permit direct transmission of data to other external devices via the public switched telephone network (PSTN) or other interconnection lines, such as a T1 lines or fiber optic cables. The information may be sent, e.g., to one of the aforementioned Merlin systems. Collectively, the stroke questionnaire generator and the stroke score determination/warning unit provide a stroke confirmation system to confirm the stroke within the patient. As already explained, in many implementations, a stroke score is not necessarily calculated. Rather, a simpler stroke questionnaire is used to confirm the stroke where any affirmative answer (indicative of a stroke related deficit) is sufficient to corroborate the stroke.

The bedside monitor may also receive diagnostic information from the implantable monitor via the telemetry system for forwarding to the patient's physician or to the Merlin system. Patient diagnostic information includes, for example, recorded ECG data. Device diagnostic data includes, for example, information representative of the operation of the implanted device such as battery voltages, battery recommended replacement time (RRT) information and the like. Data retrieved from the implanted devices is stored by bedside monitor 12 either within a random access memory (RAM) 530, hard drive 508 or within a floppy diskette placed within floppy drive 526. Additionally, or in the alternative, data may be permanently or semi-permanently stored within a compact disk (CD) or other digital media disk, if the overall system is configured with a drive for recording data onto digital media disks, such as a write once read many (WORM) drive.

The above-described stroke detection techniques can also be implemented using a pacer/ICD by exploiting IEGM signals, rather than ECG signals. For the sake of completeness, an exemplary pacer/ICD will now be described in detail.

Exemplary Pacemaker/ICD

Figure 7:
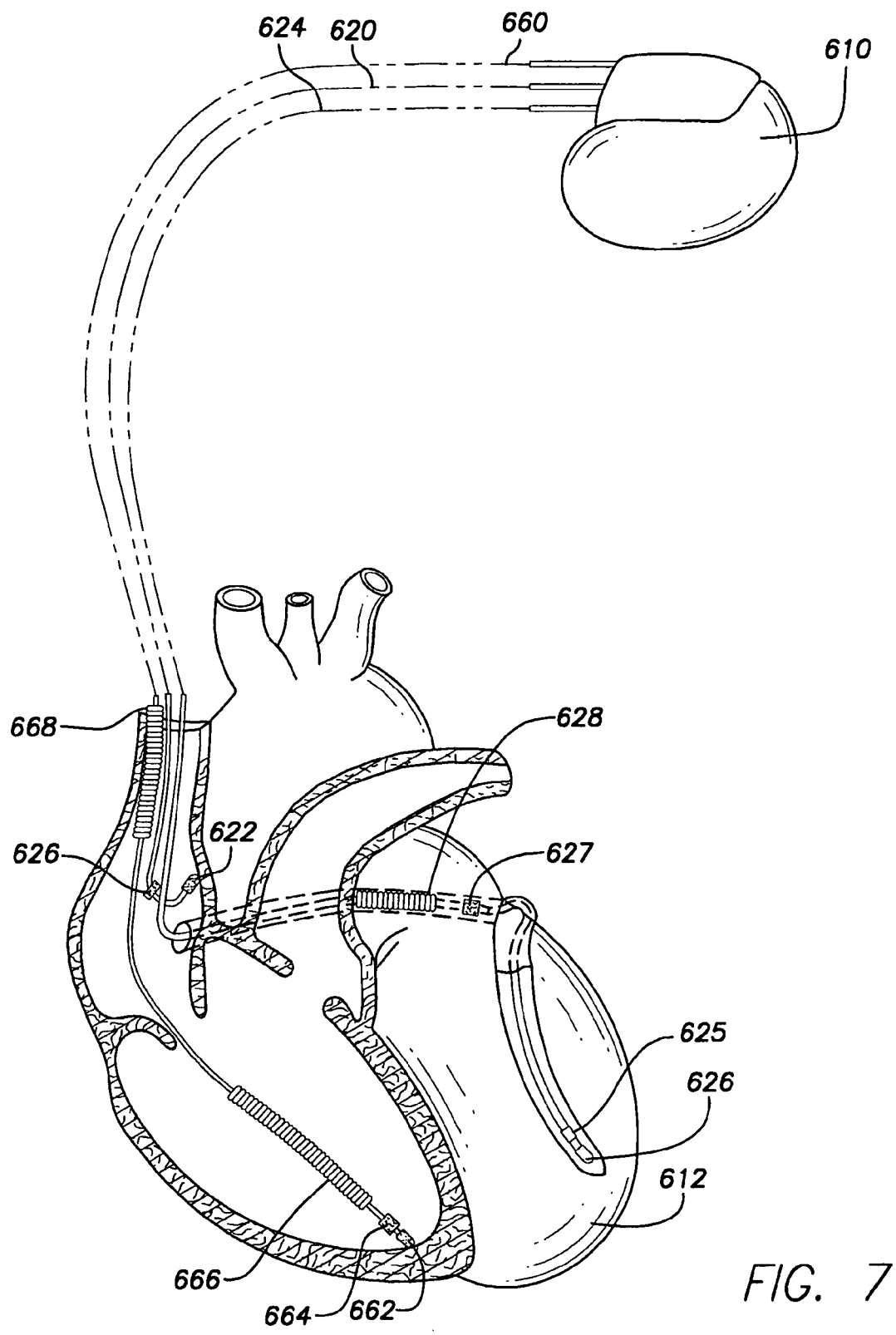
FIG. 7 is a simplified, partly cutaway view of the heart of a patient, illustrating an exemplary pacer/ICD, along with a set of leads implanted in the heart of the patient, for use with an alternative IEGM-based stroke detection implementation.
Figure 8:
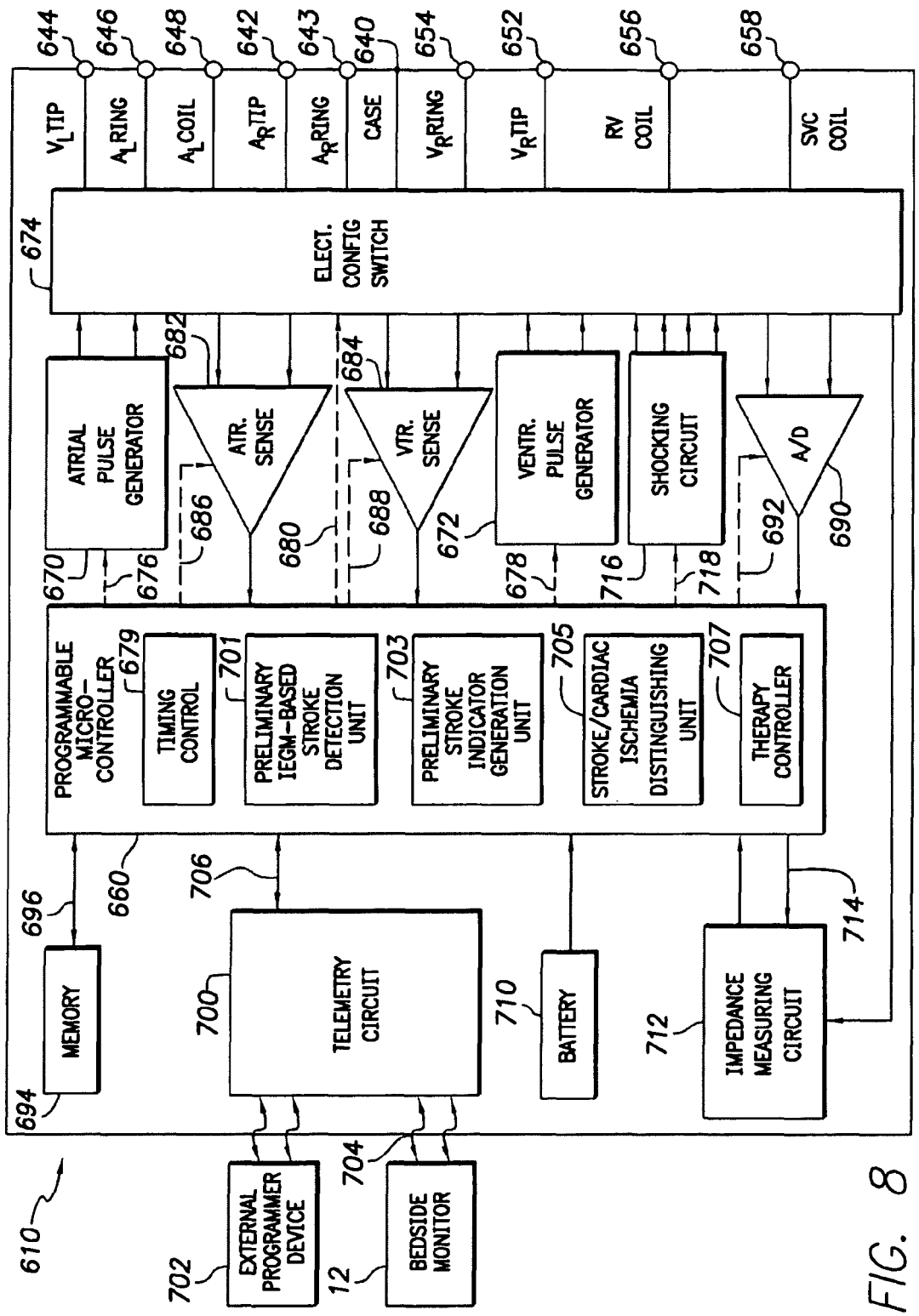
FIG. 8 is a functional block diagram of the pacer/ICD of FIG. 7, illustrating basic device circuit elements that provide cardioversion, defibrillation and/or pacing stimulation in four chambers of the heart and particularly illustrating components within the device for detecting a preliminary indication of stroke based on an analysis of the IEGM of the patient.

With reference to FIGS. 7 and 8, a description of an exemplary pacer/ICD will now be provided, which is equipped to detect a possible stroke within the patient based on an analysis of the IEGM of the patient. FIG. 7 provides a simplified block diagram of the pacer/ICD, which is a dual-chamber stimulation device capable of treating both fast and slow arrhythmias with stimulation therapy, including cardioversion, defibrillation, and pacing stimulation. To provide atrial chamber pacing stimulation and sensing, pacer/ICD 610 is shown in electrical communication with a heart 612 by way of a left atrial lead 620 having an atrial tip electrode 622 and an atrial ring electrode 623 implanted in the atrial appendage. Pacer/ICD 610 is also in electrical communication with the heart by way of a right ventricular lead 630 having, in this embodiment, a ventricular tip electrode 632, a right ventricular ring electrode 634, a right ventricular (RV) coil electrode 636, and a superior vena cava (SVC) coil electrode 638. Typically, the right ventricular lead 630 is transvenously inserted into the heart so as to place the RV coil electrode 636 in the right ventricular apex, and the SVC coil electrode 638 in the superior vena cava. Accordingly, the right ventricular lead is capable of receiving cardiac signals, and delivering stimulation in the form of pacing and shock therapy to the right ventricle.

To sense left atrial and ventricular cardiac signals and to provide left chamber pacing therapy, pacer/ICD 610 is coupled to a CS lead 624 designed for placement in the "CS region" via the CS os for positioning a distal electrode adjacent to the left ventricle and/or additional electrode(s) adjacent to the left atrium. As used herein, the phrase "CS region" refers to the venous vasculature of the left ventricle, including any portion of the CS, great cardiac vein, left marginal vein, left posterior ventricular vein, middle cardiac vein, and/or small cardiac vein or any other cardiac vein accessible by the CS. Accordingly, an exemplary CS lead 624 is designed to receive atrial and ventricular cardiac signals and to deliver left ventricular pacing therapy using at least a left ventricular tip electrode 626, left atrial pacing therapy using at least a left atrial ring electrode 627, and shocking therapy using at least a left atrial coil electrode 628. With this configuration, biventricular pacing can be performed. Although only three leads are shown in FIG. 6, it should also be understood that additional stimulation leads (with one or more pacing, sensing and/or shocking electrodes) might be used in order to efficiently and effectively provide pacing stimulation to the left side of the heart or atrial cardioversion and/or defibrillation.

A simplified block diagram of internal components of pacer/ICD 610 is shown in FIG. 8. While a particular pacer/ICD is shown, this is for illustration purposes only, and one of skill in the art could readily duplicate, eliminate or disable the appropriate circuitry in any desired combination to provide a device capable of treating the appropriate chamber(s) with cardioversion, defibrillation and pacing stimulation as well as providing for the aforementioned stroke detection.

The housing or case of 640 for pacer/ICD 610, shown schematically in FIG. 8, is often referred to as the "can", "case" or "case electrode" and may be programmably selected to act as the return electrode for all "unipolar" modes. The housing 640 may further be used as a return electrode alone or in combination with one or more of the coil electrodes, 628, 636 and 638, for shocking purposes. The housing 640 further includes a connector (not shown) having a plurality of terminals, 642, 643, 644, 646, 648, 652, 654, 656 and 658 (shown schematically and, for convenience, the names of the electrodes to which they are connected are shown next to the terminals). As such, to achieve right atrial sensing and pacing, the connector includes at least a right atrial tip terminal ($A_R$ TIP) 642 adapted for connection to the atrial tip electrode 622 and a right atrial ring ($A_R$ RING) electrode 643 adapted for connection to right atrial ring electrode 623. To achieve left chamber sensing, pacing and shocking, the connector includes at least a left ventricular tip terminal ($V_L$ TIP) 644, a left atrial ring terminal ($A_L$ RING) 646, and a left atrial shocking terminal ($A_L$ COIL) 648, which are adapted for connection to the left ventricular ring electrode 626, the left atrial ring electrode 627, and the left atrial coil electrode 628, respectively. To support right chamber sensing, pacing and shocking, the connector further includes a right ventricular tip terminal ($V_R$ TIP) 652, a right ventricular ring terminal ($V_R$ RING) 654, a right ventricular shocking terminal ($V_R$ COIL) 656, and an SVC shocking terminal (SVC COIL) 658, which are adapted for connection to the right ventricular tip electrode 632, right ventricular ring electrode 634, the $V_R$ coil electrode 636, and the SVC coil electrode 638, respectively.

At the core of pacer/ICD 610 is a programmable microcontroller 660, which controls the various modes of stimulation therapy. As is well known in the art, the microcontroller 660 (also referred to herein as a control unit) typically includes a microprocessor, or equivalent control circuitry, designed specifically for controlling the delivery of stimulation therapy and may further include RAM or ROM memory, logic and timing circuitry, state machine circuitry, and I/O circuitry. Typically, the microcontroller 660 includes the ability to process or monitor input signals (data) as controlled by a program code stored in a designated block of memory. The details of the design and operation of the microcontroller 660 are not critical to the invention. Rather, any suitable microcontroller 660 may be used that carries out the functions described herein. The use of microprocessor-based control circuits for performing timing and data analysis functions are well known in the art.

As shown in FIG. 8, an atrial pulse generator 670 and a ventricular pulse generator 672 generate pacing stimulation pulses for delivery by the right atrial lead 620, the right ventricular lead 630, and/or the CS lead 624 via an electrode configuration switch 674. It is understood that in order to provide stimulation therapy in each of the four chambers of the heart, the atrial and ventricular pulse generators, 670 and 672, may include dedicated, independent pulse generators, multiplexed pulse generators or shared pulse generators. The pulse generators, 670 and 672, are controlled by the microcontroller 660 via appropriate control signals, 676 and 678, respectively, to trigger or inhibit the stimulation pulses.

The microcontroller 660 further includes timing control circuitry (not separately shown) used to control the timing of such stimulation pulses (e.g., pacing rate, AV delay, atrial interconduction (inter-atrial) delay, or ventricular interconduction (V-V) delay, etc.) as well as to keep track of the timing of refractory periods, blanking intervals, noise detection windows, evoked response windows, alert intervals, marker channel timing, etc., which is well known in the art. Switch 674 includes a plurality of switches for connecting the desired electrodes to the appropriate I/O circuits, thereby providing complete electrode programmability. Accordingly, the switch 674, in response to a control signal 680 from the microcontroller 660, determines the polarity of the stimulation pulses (e.g., unipolar, bipolar, combipolar, etc.) by selectively closing the appropriate combination of switches (not shown) as is known in the art.

Atrial sensing circuits 682 and ventricular sensing circuits 684 may also be selectively coupled to the right atrial lead 620, CS lead 624, and the right ventricular lead 630, through the switch 674 for detecting the presence of cardiac activity in each of the four chambers of the heart. Accordingly, the atrial (ATR. SENSE) and ventricular (VTR. SENSE) sensing circuits, 682 and 684, may include dedicated sense amplifiers, multiplexed amplifiers or shared amplifiers. The switch 674 determines the "sensing polarity" of the cardiac signal by selectively closing the appropriate switches, as is also known in the art. In this way, the clinician may program the sensing polarity independent of the stimulation polarity. Each sensing circuit, 682 and 684, preferably employs one or more low power, precision amplifiers with programmable gain and/or automatic gain control and/or automatic sensitivity control, bandpass filtering, and a threshold detection circuit, as known in the art, to selectively sense the cardiac signal of interest. The automatic gain/sensitivity control enables pacer/ICD 610 to deal effectively with the difficult problem of sensing the low amplitude signal characteristics of atrial or ventricular fibrillation. The outputs of the atrial and ventricular sensing circuits, 682 and 684, are connected to the microcontroller 660 which, in turn, are able to trigger or inhibit the atrial and ventricular pulse generators, 670 and 672, respectively, in a demand fashion in response to the absence or presence of cardiac activity in the appropriate chambers of the heart.

For arrhythmia detection, pacer/ICD 610 utilizes the atrial and ventricular sensing circuits, 682 and 684, to sense cardiac signals to determine whether a rhythm is physiologic or pathologic. As used herein "sensing" is reserved for the noting of an electrical signal, and "detection" is the processing of these sensed signals and noting the presence of an arrhythmia. The timing intervals between sensed events (e.g., P-waves, R-waves, and depolarization signals associated with fibrillation which are sometimes referred to as "F-waves" or "Fib-waves") are then classified by the microcontroller 660 by comparing them to a predefined rate zone limit (i.e., bradycardia, normal, atrial tachycardia, atrial fibrillation, low rate VT, high rate VT, and fibrillation rate zones) and various other characteristics (e.g., sudden onset, stability, physiologic sensors, and morphology, etc.) in order to determine the type of remedial therapy that is needed (e.g., bradycardia pacing, antitachycardia pacing, cardioversion shocks or defibrillation shocks).

Cardiac signals are also applied to the inputs of an analog-to-digital (A/D) data acquisition system 690. The data acquisition system 690 is configured to acquire intracardiac electrogram signals, convert the raw analog data into a digital signal, and store the digital signals for later processing and/or telemetric transmission to an external device 702. The data acquisition system 690 is coupled to the right atrial lead 620, the CS lead 624, and the right ventricular lead 630 through the switch 674 to sample cardiac signals across any pair of desired electrodes. The microcontroller 660 is further coupled to a memory 694 by a suitable data/address bus 696, wherein the programmable operating parameters used by the microcontroller 660 are stored and modified, as required, in order to customize the operation of pacer/ICD 610 to suit the needs of a particular patient. Such operating parameters define, for example, pacing pulse amplitude or magnitude, pulse duration, electrode polarity, rate, sensitivity, automatic features, arrhythmia detection criteria, and the amplitude, waveshape and vector of each shocking pulse to be delivered to the patient's heart within each respective tier of therapy. Other pacing parameters include base rate, rest rate and circadian base rate.

Advantageously, the operating parameters of the implantable pacer/ICD 610 may be non-invasively programmed into the memory 694 through a telemetry circuit 724 in telemetric communication with the external device 702, such as a programmer, transtelephonic transceiver or a diagnostic system analyzer. The telemetry circuit 724 is activated by the microcontroller by a control signal 706. The telemetry circuit 724 advantageously allows intracardiac electrograms and status information relating to the operation of pacer/ICD 610 (as contained in the microcontroller 660 or memory 694) to be sent to the external device 702 through an established communication link 704. The telemetry circuit also transmits signals to bedside monitor 12, including the aforementioned stroke indication signal.

Pacer/ICD 610 further includes an accelerometer or other physiologic sensor 708, commonly referred to as a "rate-responsive" sensor because it is typically used to adjust pacing stimulation rate according to the exercise state of the patient. However, the physiological sensor 708 may further be used to detect changes in cardiac output, changes in the physiological condition of the heart, or diurnal changes in activity (e.g., detecting sleep and wake states) and to detect arousal from sleep. Accordingly, the microcontroller 660 responds by adjusting the various pacing parameters (such as rate, AV delay, V-V delay, etc.) at which the atrial and ventricular pulse generators, 670 and 672, generate stimulation pulses. While shown as being included within pacer/ICD 610, it is to be understood that the physiologic sensor 708 may also be external to pacer/ICD 610, yet still be implanted within or carried by the patient. A common type of rate responsive sensor is an activity sensor incorporating an accelerometer or a piezoelectric crystal, which is mounted within the housing 640 of pacer/ICD 610. Other types of physiologic sensors are also known, for example, sensors that sense the oxygen content of blood, respiration rate and/or minute ventilation, pH of blood, ventricular gradient, etc.

The pacer/ICD additionally includes a battery 726, which provides operating power to all of the circuits shown in FIG. 8. The battery 726 may vary depending on the capabilities of pacer/ICD 610. For pacer/ICD 610, which employs shocking therapy, the battery 726 should be capable of operating at low current drains for long periods, and then be capable of providing high-current pulses (for capacitor charging) when the patient requires a shock pulse. The battery 726 must also have a predictable discharge characteristic so that elective replacement time can be detected. Accordingly, pacer/ICD 610 is preferably capable of high voltage therapy and appropriate batteries.

As further shown in FIG. 8, pacer/ICD 610 is shown as having an impedance measuring circuit 712 which is enabled by the microcontroller 660 via a control signal 714. Uses for an impedance measuring circuit include, but are not limited to, lead impedance surveillance during the acute and chronic phases for proper lead positioning or dislodgement; detecting operable electrodes and automatically switching to an operable pair if dislodgement occurs; measuring respiration or minute ventilation; measuring thoracic impedance for determining shock thresholds; detecting when the device has been implanted; and detecting the opening of heart valves, etc. The impedance measuring circuit 120 is advantageously coupled to the switch 74 so that any desired electrode may be used.

In the case where pacer/ICD 610 is intended to operate as an implantable cardioverter/defibrillator (ICD) device, it detects the occurrence of an arrhythmia, and automatically applies an appropriate electrical shock therapy to the heart aimed at terminating the detected arrhythmia. To this end, the microcontroller 660 further controls a shocking circuit 716 by way of a control signal 718. The shocking circuit 716 generates shocking pulses of low (up to 0.5 joules), moderate (0.5-10 joules) or high energy (11 to 40 or more joules), as controlled by the microcontroller 660. Such shocking pulses are applied to the heart of the patient through at least two shocking electrodes, and as shown in this embodiment, selected from the left atrial coil electrode 628, the RV coil electrode 636, and/or the SVC coil electrode 638. The housing 640 may act as an active electrode in combination with the RV electrode 636, or as part of a split electrical vector using the SVC coil electrode 638 or the left atrial coil electrode 628 (i.e., using the RV electrode as a common electrode). Cardioversion shocks are generally considered to be of low to moderate energy level (so as to minimize pain felt by the patient), and/or synchronized with an R-wave and/or pertaining to the treatment of tachycardia. Defibrillation shocks are generally of moderate to high energy level (i.e., corresponding to thresholds in the range of 7-40 or more joules), delivered asynchronously (since R-waves may be too disorganized), and pertaining exclusively to the treatment of fibrillation. Accordingly, the microcontroller 660 is capable of controlling the synchronous or asynchronous delivery of the shocking pulses.

Insofar as stroke detection is concerned, the microcontroller includes a preliminary IEGM-based stroke detection unit 701 operative to detect a preliminary indication of stroke based on an analysis of the IEGM of the patient, including T-waves, U-waves (if present), ST segments, and QT segments. The microcontroller also includes a preliminary stroke indicator generation unit 703, which is operative to generate the stroke indication signal for forwarding to the bedside monitor. In some implementations, a stroke/cardiac ischemia distinguishing unit 705 is provided for automatically distinguishing stroke from cardiac ischemia based on an analysis of the IEGM. A therapy controller 707 controls therapy, when appreciate, based on the detection of stroke, cardiac ischemia or other medical conditions. As one example, the pacing rate being applied to the heart may be reduced in response to a stroke so as to reduce the risk of exacerbating the stroke.

Depending upon the implementation, the various components of the microcontroller may be implemented as separate software modules or the modules may be combined to permit a single module to perform multiple functions. In addition, although shown as being components of the microcontroller, some or all of these components may be implemented separately from the microcontroller, using ASICs or the like.

The principles of the invention may be exploiting using other implantable systems or in accordance with other techniques. Thus, while the invention has been described with reference to particular exemplary embodiments, modifications can be made thereto without departing from scope of the invention. Note also that the term "including" as used herein is intended to be inclusive, i.e. "including but not limited to."

What is claimed is:

1. A method for use with an implantable medical device for implant within a patient, the method comprising:
   sensing electrocardiac signals using the implantable device;
   detecting an indication of stroke within the patient based on predetermined changes in the electrocardiac signal; and
   controlling at least one diagnostic-based device function in response the indication of the stroke.

2. The method of claim 1 wherein detecting an indication of stroke includes detecting predetermined dynamic trends in the electrocardiac signal indicative of stroke.

3. The method of claim 1 wherein detecting the indication of stroke includes detecting one more of the onset of prominent U-waves, the onset of notched T-waves, changes in ST segment duration, and changes in QT duration.

4. The method of claim 3 wherein detecting the indication of stroke includes detecting trends toward one more of increasingly prominent U-waves, increasingly notched T-waves, changing ST segment durations, and changing QT durations.

5. The method of claim 1 for use with an external system wherein detecting the indication of stroke includes:

detecting a preliminary indication of a possible stroke based on the electrocardiac signals using the implantable device;

transmitting a signal indicative of a possible stroke from the implantable device to the external system;

a generating a questionnaire using the external system for confirming the stroke within the patient;

inputting answers to the questionnaire to confirm the stroke; and outputting a warning signal from the external system upon confirmation of a stroke within the patient.

6. The method of claim 5 wherein the questionnaire includes questions directed to one or more of: balance, speech, weakness/numbness, vision and severity of headache.

7. The method of claim 5 wherein the questionnaire includes questions directed to providing a quantitative measure of stroke-related neurologic deficit.

8. The method of claim 7 wherein the questionnaire includes questions drawn from one or more preselected stroke score questionnaires.

9. The method of claim 5 wherein outputting a warning signal includes outputting a signal to notify emergency personnel upon confirmation of a stroke.

10. The method of claim 1 wherein detecting stroke based on predetermined changes in the electrocardiac signal includes:

detecting a preliminary indication of a possible stroke based on the electrocardiac signal; and distinguishing stroke from ischemia based on predetermined changes in the electrocardiac signal unique to stroke.

11. The method of claim 1 wherein controlling at least one device function in response the indication of the stroke includes generating an output signal indicative of stroke.

12. The method of claim 1 wherein sensing the electrocardiac signals includes sensing signals representative of an electrocardiogram (ECG).

13. The method of claim 12 wherein the implantable device is a subcutaneously-implantable monitoring device and wherein sensing the electrocardiac signals sensed is performed to sense signals representative of the ECG using the subcutaneously-implantable monitoring device.

14. The method of claim 1 wherein sensing the electrocardiac signals includes sensing signals representative of an intracardiac electrogram (IEGM).

15. The method of claim 1 wherein the implantable device includes an implantable cardiac rhythm management device and wherein sensing the electrocardiac signals sensed is performed to sense signals representative of the IEGM using the implantable cardiac rhythm management device.

16. A system for use with an implantable medical device for implant within a patient, the system comprising:

a electrocardiac signal sensing device for implant within the patient;

an on-board stroke detector within the implantable medical device and operative to detect an indication of stroke within the patient based on predetermined changes in the electrocardiac signals indicative of stroke; and a controller within the implantable medical device that is responsive to an indication of stroke to control one or more diagnostic-based device functions.

17. The system of claim 16 wherein the stroke detector comprises:

a preliminary ECG-based stroke detection unit; and a preliminary stroke detection indicator generation unit.

18. A system for use with an implantable medical device for implant within a patient, the system comprising:

means for sensing electrocardiac signals using the implantable device;

means for detecting an indication of stroke within the patient based on predetermined changes in the electrocardiac signal; and means for controlling at least one diagnostic-based device function in response to the indication of stroke.

* * * * *